(12) United States Patent
Spinella

(10) Patent No.: US 6,461,814 B1
(45) Date of Patent: Oct. 8, 2002

(54) METHOD OF IDENTIFYING GENE TRANSCRIPTION PATTERNS

(76) Inventor: Dominic G. Spinella, 7026 Via Calafia, La Costa, CA (US) 92009

( * ) Notice: Subject to any disclaimer, the term of this patent is extended or adjusted under 35 U.S.C. 154(b) by 0 days.

(21) Appl. No.: 09/263,196

(22) Filed: Mar. 5, 1999

Related U.S. Application Data

(63) Continuation-in-part of application No. 08/784,208, filed on Jan. 15, 1997, now Pat. No. 5,968,784.

(51) Int. Cl.$^7$ .................................................. C12Q 1/68
(52) U.S. Cl. ......................... 435/6; 435/91.1; 435/183; 435/320.1; 536/23.5
(58) Field of Search ........................ 435/6, 91.1, 91.2, 435/183, 287.2, 320.1; 436/694; 536/23.5

(56) References Cited

U.S. PATENT DOCUMENTS

| | | |
|---|---|---|
| 4,900,811 A | 2/1990 | Sutcliffe |
| 5,202,231 A | 4/1993 | Drmanac et al. |
| 5,242,798 A | 9/1993 | Sutcliffel |
| 5,474,914 A | * 12/1995 | Spaete ........................ 435/69.1 |
| 5,508,169 A | 4/1996 | Deugau et al. |
| 5,656,425 A | 8/1997 | Kraus |
| 5,700,644 A | 12/1997 | Gould et al. |

FOREIGN PATENT DOCUMENTS

| | | |
|---|---|---|
| EP | 0234781 | 2/1987 |
| EP | 0761822 | 3/1997 |
| WO | 9513369 | 5/1995 |
| WO | 9520681 | 8/1995 |
| WO | 9814619 | 4/1998 |

OTHER PUBLICATIONS

Promega Catalog, pp. 38–41, 89–90, and 108–119, 1993/1994.*

Stratagene catalog, 1993, pp. 142, 193, 199, and 151–154.*

Adams et al., "Sequence identification of 2,375 human brain genes" Nature 355: 632–634, 1992.

Adams, M.D. et al. "Initial assessment of human gene diversity and expression patterns based upon 83 million nucleotides of cDNA sequence", Nature 377: (Suppl.) 3: 1995.

Adams et al., "Complimentary DNA Sequencing: Expressed Sequence Tags and Human Genome Project", Science 252, 1651–1656, 1996.

Andersson et al., "Simultaneous Shotgun Sequencing of Multiple cDNA Clones," DNA Sequence—The Journal of Sequencing and Mapping 7(2): 63–70.

Aviv and Ledger, "Purification of Biologicially Active Globin Messenger RNA by Chromatography on Oligothymidylic acid–Cellulose," Proc Natl. Acad. Sci, USA 69: 1408–1412, 1972.

Brenner and Livak "DNA fingerprinting by sampled sequencing," Proc. Natl. Acad. Sci. USA 86: 8902–8906, 1989.

Cease & Cortland, "A Vector for Facile PCR Product Cloning and Modification Generating Any Desired 4–Base 5' Overhang; pRPM," Biotechniques, 14(2): 250–255, 1993.

Chollet and Kawashima, "Biotin–labeled synthetic oligodeoxyribonucleotides: chemical synthesis and uses as hybridization probes," Nucleic Acids Research 13(5): 1529–1541, 1985.

Crystal, "Transfer of Genes to Humans: Early Lessons and Obstacles to Success," Science 270: 404–410, 1995.

Fields et al., "How many genes in the human genome?" Nature Genetics 7: 345–346, 1994.

Fleischmann et al., "Whole–Genome Random Sequencing and Assembly of *Haemophilus influenzae* Rd," Science 269: 496–512, 1995.

Fraser et al., "The Minimal Gene Compliment of *Mycoplasma genitalium*," Science 270: 397–403, 1995.

Ghosh and Musso, "Covalent attachment of oligonucleotides to solid supports," Nucleic Acids Research 15(13): 5353–5372, 1987.

Gilliand et al., "Ch. 8: Competitive PCR for Quantitation of mRNA," in PCR Protocols: A Guide to Methods and Applications, Academic Press, Inc., pp. 60–69, 1990.

Goffeau, "Life with 482 Genes," Science 270: 445–446, 1995.

Gubler and Hoffman, "A simple and very efficient method for generating cDNA libraries," Gene 25: 263–269, 1983.

Hasan et al., "A novel multistep method for generating precise unidirectional deletions using BspMI, a cass–IIS restriction enzyme," Gene 50: 55–62, 1986.

Hodgkin et al., "The Nematode *Caenorhabditis elegans* and Its Genome," Science 270: 410–414, 1995.

Huynh, T.V. et al. DNA Cloning, A Practical Approach, D. Glover Ed, 1984.

Ivanova et al., "Novel Method of Comparative Gene Expression Analysis and Identification of Differentially Expressed mRNAs," Molecular Biology 28(6): 848–853, 1995.

Jones, "An Alternative and Regenerative Method of DNA Sequencing," Biotechniques 22(5): 938–946, 1997.

Kahn, "From Genome to Proteins: Looking at a Cell's Proteins," Science 270: 369–370, 1995.

Kaiser and Murray, "The Use of Phage Lambda Replacement Vectors in the Construction of Representative Genomic DNA Libraries," DNA Cloning: A Practical Approach, Edited by DM Glover, 1: 1–48.

(List continued on next page.)

Primary Examiner—Bradley L. Sisson
(74) Attorney, Agent, or Firm—Richard A. Hake

(57) ABSTRACT

This invention provides an rapid, artifact free, improved method of obtaining short DNA "tag" or arrays thereof, allowing for determination of the relative abundance of a gene transcript within a given mRNA population and is useful to identify patterns of gene transcription, as well as identify new genes.

8 Claims, No Drawings

OTHER PUBLICATIONS

Kato, K., "Description of the entire mRNA population by a 3' end cDNA fragment generated by clas IIS restriction enzymes," Nucleic Acids Research 23(18): 3685–3690, 1995.

Lambda ZAP Express—Internet—http://biology.quensu.ca/~ miseners/vector_descrip.

Lee et al., "Positive Selection of Candidate Tumor Suppressor Genes by Subtractive Hybridization," Proc. Natl. Acad. Sci. USA, 88: 2825–2829, 1991.

Lee et al., "Sequential amplification of clone DNA as tandem multimer using class–IIS restriction enzymes," Genetic Analysis: Biomolecular Engineering 13: 139–145, 1996.

Liang and Pardee, "Differential Display of Eukaryotic Messender RNA by Means of the Polymerase Chain Reaction" Science 257: 967–971, 1992.

Liang et al., "Distribution and cloning of eukaryotic mRNAs by means of differential display: reginements and optimization," Nucleic Acids Research 14: 3269–3275, 1993.

Maniatis et al., "The Isolation of Structural Genes from Libraries of Eucaryotic DNA," Cell 15: 687–701, 1978.

Mormeneo et al., "Precise nucleotide sequence modifications with bidirectionally cleaving class–IIS excision linkers," Gene 61: 21–30, 1987.

Nadeau et al., "Multilocus markers for mouse genome analysis: PCR amplification based on single primers of arbitrary nucelotide sequence," Mannalian Genome 3: 55–64, 1992.

Nowak, "Entering the Postgenome Era," Science 270: 368–369, 1995.

Okubo, K et al. Nature Genetics 2: 173–179, 1992.

Olson, "A Time to Sequence," Science 270: 394–396, 1995.

Podhajska et al., "Conferring New Specificities on Restriction Enzymes: Cleavage at Any Predetermined Site by Combining Adapter Oligodexynucleotide and Class–IIS Enzyme," Methods in Enzymology 216: 303–309, 1992.

Ramsey, G. "DNA Chips: State–of–the–art," Nature Biotechnology, 16: 40–44, 1998.

Research Genetics (advertisement), Nucleic Acids Research, vol. 22, No. 15, Aug. 11, 1994.

Sambrook et al., "Ch. 7—Extraction, Purification, and Analysis of Messenger RNA from lukaryotic Cells," in Molecular Cloning: A Laboratory Manual, $2^{nd}$ edition, vol. 1, Cold Springs Harbor Laboratory Press, pp. 7.1–7.87, 9.51, 11.46–47, 1989.

Schena et al., "Quantitative Monitoring of Gene Expression Patterns with a Complementary DNA Microarray," Science 270:467–470, 1995.

Sigma Molecular Biology (catalog), pp. 42, 43 and 108, 1989.

Smith et al., "The synthesis of oligonucleotides containing an aliphatic amino group at the 5' terminus: synthesis of flourescent DNA primers for use in DNA sequence analysis," Nucleic Acids Research 13(7): 2399–2412, 1985.

Stratagene Cloning Systems, Product Catalog, p. 91, 1999.

Szybalski, W., "Universal restriction endonucleases: designing novel cleavage specificities by combiing dapter oligodexynucleotide and enzyme moieties," Gene 40: 169–173, 1985.

Szybalski et al., "Class IIS restriction enzymes—a review," Gene 100: 13–26, 1991.

Unrau and Deugau, "Non–cloning amplification of specific DNA fragments from whole genomic DNA digests using DNA 'indexers'," Gene 145: 163–169, 1994.

Velculescu et al., "Serial Analysis of Gene Expression," Science 270: 484–487, 1995.

Velculescu V.E. et al, "Characterization of the Yeast Transcriptome" Cell: vol. 88: 243–251.

Villarreal and Long, "A General Method of Polymerase–Chain–Reaction–Enabled Protein Domain Mutagenesis: Construction of a Human Protein S–Osteonectin Gene".

Vos, P. et al. "AFLP: A new technique for DNA fingerprinting", Nucleic Acids Res. 23: 4407–4414, 1995.

Welsh and McClelland, "Fingerprinting genomes using PCER with arbitrary primers," Nucleic Acids Research 18: 7213–7218, 1990.

Welsh et al., "Arbitrarily primed PCR fingerprinting of RNA," Nucleic Acids Research 20: 4965–4970, 1992.

White et al., "The polymerase chain reaction," Trends in Genetics, 5(6): 185–189, 1989.

White et al., "Concatemer Chain Reaction: A Tag DNA Polymerase–Medicated Mechanism for Generating Long Tandemly Repetive DNA Sequences," Analytical Biochemistry 199: 184–190, 1991.

Williams, "DNA polymorphisms amplified by arbitrary primers are useful as genetic markers," Nucleic Acids Research 18: 6531–6535, 1990.

Woodward et al., "Random sequence oligonucleotide primers detect polymorphic DNA products which segregate in inbred strains of mice," Mammalian Genome 3: 73–78, 1992.

\* cited by examiner

METHOD OF IDENTIFYING GENE TRANSCRIPTION PATTERNS

CROSS REFERENCE TO RELATED APPLICATIONS

This application is a continuation in part of application Ser. No. 08/784,208, filed Jan. 15, 1997, now U.S. Pat. No. 5,968,784, issued Oct. 19, 1999.

FIELD OF THE INVENTION

This invention relates to a method of identifying gene transcription patterns in a cell or tissue.

BACKGROUND OF THE INVENTION

Expressed Sequence Tag (EST) programs have provided DNA sequence information for a substantial proportion of expressed human genes (Fields, C. et al., *Nature Genetics* 7: 345–346 (1994)) in the human genome. However, DNA sequence information alone is insufficient for a complete understanding of gene function and regulation.

Because only a fraction of the full genetic repertoire is expressed in a cell at any given time, and because gene expression effects cell phenotype, tools to qualitatively and quantitatively monitor gene transcription are needed.

Classical qualitative and quantitative techniques such as northern blotting and nuclease protection assays are accurate and quantitative, but cannot provide information quickly enough to generate global gene expression profiles.

More recent approaches include sequence analysis of random isolates from cDNA libraries, Polymerase Chain Reaction (PCR) and hybridization-array-based methodologies, but each of these methods has limitations.

High-density microarray hybridization of RNA or cDNA corresponding to known genes (Ramsay, G. *Nature Biotechnology* 16: 40–44 (1998)) is a fast method for parallel analysis of global gene expression. This method, however, is limited to known genes and the number of genes in a single microarray is limited as well.

Sequencing of random isolates from cDNA libraries to generate ESTs provides quantitative results, but is a daunting task. (Adams, M. D., et al., *Science* 252: 1651–1656 (1991); Adams, M. D. et al., *Nature* 355: 632–634 (1992)). Within cDNA libraries, the frequency of a cDNA clone should be proportional to the steady-state amount of that transcript in the RNA population of the cell or tissue from which the RNA was derived. (Okubo K. et al., *Nature Genetics* 2: 173–179 (1992); Lee, N. H. et al., *Proc Natl Acad Sci USA* 92: 8303–8307 (1995)). This approach, however, requires DNA sequencing efforts beyond the capacity of most laboratories.

PCR-based methods can generate DNA fragments from mRNA pools which differ in size and sequence enabling their separation and identification to form an expression profile. Profiles from different cell or tissue populations to detect differentially expressed genes. This method has been used to establish databases of mRNA fragments. (Williams, J. G. K., *Nucl. Acids Res.* 18:6531 (1990); Welsh, J., et al. *Nucl. Acids Res.*, 18:7213 (1990); Woodward, S. R., Mamm. Genome, 3:73 (1992); Nadeau, J. H., *Mamm. Genome* 3:55 (1992)). Some have sought to adapt these methods to compare mRNA populations between two or more samples (Liang, P. et al. *Science* 257:967 (1992); See also Welsh, J. et al., *Nucl. Acid Res.* 20:4965 (1992); Liang, P., et al., *Nucl. Acids Res.*, 3269 (1993), and WO 95/13369, Published May 18, 1995. Differential Display and Amplified Fragment Length Polymorphism (AFLP) (Liang P. and Pardee, A. B. *Science* 257: 967–971 (1992)), (Vos, P. et al., *Nucleic Acids Res.* 23: 4407–4414. (1995)), for example, can provide gene expression information at the appropriate speed and scale, but these methods can suffer from a lack of precision and reproducibility due to their susceptibility to quantitative PCR artifacts.

Recently, a variation of PCR for a random cDNA sequencing approach was described by Velculescu et al. (Velculescu, V. E. et al., *Science* 270:484 (1995)). This technique, called Serial Analysis of Gene Expression (SAGE), generates short, defined sequences from cDNAs which are randomly ligated in a tail-to-tail fashion and amplified by PCR to form "di-tags". These di-tags are then concatenated into arrays which are cloned and analyzed by DNA sequencing. Because each sequencing template contains identifiable tags corresponding to many genes, the potential throughput of SAGE exceeds traditional cDNA sequencing, allowing gene transcription profiling in many laboratories.

However, the results for SAGE, like any other PCR process is influenced by factors other than starting template abundance. Sequence-specific differences in "amplification efficiency" are known to give rise to artifactual differences in product yield. That is, the quantity of PCR product may differ in the absence of real differences in starting template. For example, amplification of the same template preparation produces product yields that can vary by as much as 6-fold (Gilliand et al. PCR Protocols. Academic Press, pp 60–69 (1990)). Hence, any PCR-based method that attempts to infer starting template abundance from the quantity of product generated by amplification requires stringent co-amplification controls.

Thus, there is a need for a simple and reproducible method for detecting and quantifying gene transcription, identifying genes, and gene transcription patterns and frequency in individual cells or tissues, which is free from PCR and other artifacts, provides for unknown genes, and yet is fast enough to allow speedy detection and comparison between samples.

In order to circumvent the problems found in the art, we have developed a cDNA tag-based technique called TAL-EST (Tandem Arrayed Ligation of Expressed Sequence Tags) that avoids PCR amplification artifacts. The technique provides a ~25-fold increase in throughput relative to random cDNA sequencing approaches to gene expression profiling.

SUMMARY OF THE INVENTION

This invention provides an improved method of obtaining short DNA "tag" sequences which allows for determination of the relative abundance of a gene transcript within a given mRNA population.

This invention provides a method of obtaining an array of tags.

This invention provides a method of identifying patterns of gene transcription.

This invention provides a method of detecting differences in gene transcription between two or more mRNA populations.

This invention provides a method of determining the frequency of individual gene transcription in an mRNA population.

This invention provides a method of screening for the effects of a drug on a cell or tissue.

This invention provides a method of detecting the presence of a stress, whether disorder, disease, the onset or proceeding of development or differentiation, exogenous substance (chemical, cofactor, biomolecule or drug), condition (including environmental conditions, such as heat, osmotic pressure, or the like), receptor activity (whether due to a ligand in a receptor or otherwise), abberant cellular condition (including mutation, unusual copy number or the like) in a target organism.

This invention provides a method of isolating a gene.

This invention provides a kit for obtaining a tag or an array of tags.

DETAILED DESCRIPTION OF THE INVENTION

To aid the skilled artisan in understanding this invention the following definitions are provided, where they deviate from the terms commonly used in the art.

"A pattern of gene transcription" as used herein, means the set of genes within a specific tissue or cell type that are transcribed or expressed to form RNA molecules. Which genes are expressed in a specific cell line or tissue and at what level the genes are expressed will depend on factors such as tissue or cell type, stage of development of the cell, tissue, or target organism and whether the cells are normal or transformed cells, such as cancerous cells. For example, a gene is expressed at the embryonic or fetal stage in the development of a specific target organism and then becomes non-expressed as the target organism matures. Or, as another example, a gene is expressed in liver tissue but not in brain tissue of an adult human. In another example, a gene is expressed at low levels in normal lung tissue but is expressed at higher levels in diseased lung tissue. "A punctuating restriction endonuclease" as used herein, means a restriction endonuclease having a probability of recognizing a sequence within each copy of cDNA. Preferably, the punctuating endonuclease recognizes a sequence consisting of less than six bases. More preferably the punctuating endonuclease recognizes a sequence consisting of four bases. Most preferably, the punctuating endonuclease is MspI, HaeIII or Sau3aI, or any isoschizomer thereof.

"A Type IIs restriction endonuclease" as used herein, means a restriction endonuclease allowing DNA cleavage at a site in the DNA distant from the recognition sequence for the restriction endonuclease. Preferably, the Type IIS restriction endonuclease recognizes four to seven bases and cleaves the adjacent DNA 10–18 bases 3' to the recognition sequence, also preferably greater than 10 bases. Hence "distant" means within the range of type IIs or type IIs-like restriction endonucleases. Most preferably, the type IIs restriction endonuclease is BsgI, BseRI, FokI, BsmFI.

"A 5' cloning restriction endonuclease" as used herein, means a restriction endonuclease having a corresponding methylase or other protection means that can protect any DNA from cleavage by the enzyme. Preferably, the 5' cloning restriction endonuclease recognizes a sequence of between about four to ten bases. Examples of this most preferably, the 5' cloning restriction endonuclease is EcoRI, BamH1, HindIII "A 3' cloning restriction endonuclease" as used herein, means a restriction endonuclease having a recognition sequence that appears infrequently in the human genome. Preferably, the 3' cloning restriction endonuclease recognizes a sequence consisting of six or more bases, preferably more than six bases. More preferably the 3' cloning restriction endonuclease recognizes a sequence consisting of eight or more bases containing a CG dinucleotide within it. More preferably, the 3' cloning restriction endonuclease provides a cleavage end that does not easily ligate to the cleavage end generated by the 5' cloning restriction enzyme. An example of a most preferred is the 3' cloning restriction endonuclease, NotI.

"A 3'-most cDNA fragment" as used herein, means a fragment of double-stranded cDNA, transcribed from an mRNA population of interest from an oligo dT primer, which is preferably biotinylated, consisting of that portion of the full length cDNA between the 3'-most punctuating restriction endonuclease site, and the 3' terminus of the cDNA. The 3'-most cDNA fragment may be isolated on a solid phase matrix containing streptavidin so as to ease its separate the fragment from other cDNA fragments produced by digestion with the punctuating restriction endonuclease.

"A first cDNA construct" as used herein, means a cDNA construct comprising the 3'-most cDNA fragment ligated to a 5' adapter. A 5' adapter is ligated to the 5' end of the cDNA fragment providing the first cDNA construct. It is preferred that this 5' adapter would provide suitable recognition sites for endonucleases envisioned to be used therein, and it is also preferable to provide sufficient molecular weight for resolution from tags, of course these requirements change with choice of enzyme, staining method for resolution, and the like. The 5' adapter may be biotinylated allowing the first cDNA construct to be captured on a solid phase matrix containing streptavidin so as to ease its isolation.

"A second cDNA construct" as used herein, means a cDNA construct provided by cleaving the first cDNA construct with a type IIs restriction endonuclease which recognizes a sequence within the 5' adapter but cuts the DNA within the cDNA fragment.

"A third cDNA construct" as used herein, means a cDNA construct comprising the second cDNA construct and a 3' adapter. A 3' adapter is ligated to the 3' end of the second cDNA construct providing the third cDNA construct. Preferably, the third cDNA construct is biotinylated and may be captured on a solid phase matrix containing streptavidin so as to ease its isolation.

"A fourth cDNA construct" as used herein, means a cDNA construct provided by cleaving the third cDNA construct with the 5' cloning restriction endonucleases and 3' cloning restriction endonuclease which recognizes sites located in the 5' and 3' adapters, respectively.

"A 5' adapter" as used herein, means an adapter consisting of a double-stranded polydeoxyribonucleotide containing a recognition sequence for a type IIs restriction endonuclease. The 5' adapter is ligated to the 5' end of the cDNA fragment (s) generated by cleavage of cDNA with the punctuating restriction endonuclease. Preferably, the 5' adapter further contains a single-stranded overhang sequence compatible with the overhang sequence produced by cleavage of a cDNA fragment with the punctuating restriction endonuclease. ("Overhang," as used herein, is defined as the effect of having a double stranded DNA, or a DNA/RNA strand that, while largely double stranded, has at one or both ends one or more unpaired or dangling bases on one or both strand, which would be paired, but for the fact that there is no complement on the other strand. Preferably, these occur where one strand has an overhang on one end and the other strand has an overhang on the other end of the double stranded DNA.) More preferably, the 5' adapter further contains a recognition sequence for a 5' cloning restriction endonuclease located 5' to the recognition sequence for the type IIs restriction endonuclease. In a 5' adapter, the 5' cloning restriction endonuclease recognition sequence is located greater than about four, preferably greater than about 10, more preferably greater than about twenty, most preferably greater than about 30, and preferably less than about 90, more preferably less than about 70, most preferably less than about 60, nucleotides 5' to the type IIs restriction endonuclease cleavage sequence. By ligating to a cDNA fragment, a 5' adapter re-creates a recognition sequence for the punctuating restriction endonuclease. Sense strand of the 5' adapter has preferably a sequence shown in SEQ ID NO.1 and antisense strand of the 5' adapter has preferably a sequence shown in SEQ ID NO. 2.

"A 3' adapter" as used herein, means an adapter consisting of a double-stranded polydeoxyribonucleotide for ligation to the 3' end of a second cDNA construct providing a third cDNA construct. Preferably, a 3' adapter comprises a degenerate single-stranded end compatible with all possible ends of the second cDNA construct produced by a digestion with the type IIs restriction endonuclease. More preferably, a 3' adapter further contains a recognition sequence for the punctuating restriction endonuclease located 3' to the degenerate end. In the 3' adapter, the recognition sequence of the punctuating restriction endonuclease is preferably adjacent to the degenerate single-stranded end compatible with ends of the second cDNA construct produced by the type IIs restriction endonuclease. Preferably, a 3' adapter further comprises a recognition sequence for a 3' cloning restriction endonuclease located 3' to the recognition sequence for the punctuating restriction endonuclease. Preferably, the 3' adapter contains one or more biotin molecules located 3' to the recognition sequence for the 3' cloning restriction endonuclease where the 3' restriction endonuclease is not the sense strand of the 3' adapter comprises all or part of SEQ ID NO. 3 preferably is SEQ ID NO. 3 and antisense strand of the 3' adapter comprises all or part of SEQ ID NO. 4, and more preferably is SEQ ID NO. 4.

"A tag" as used herein, means a DNA a sequence consisting of:
(1) preferably double-stranded 10–14 deoxyribonucleotides corresponding to a cDNA sequence located proximal to the 3'-most punctuating restriction endonuclease site in the cDNA,
(2) a double-stranded base-pair flanking both ends of the cDNA-derived sequence which is itself derived from the recognition sequence from the punctuating restriction endonuclease, and optionally
(3) single-stranded overhang sequences derived from the punctuating restriction endonuclease generating self-compatible cohesive ends.

Before amplification, one tag represents one copy of mRNA and no two same tags are created from one copy of mRNA. A tag comprises cDNA sequences. Preferably, the tags are ligated together using DNA ligase. Treatment of tag ends may be either blunt or cohesive with overhangs. For reasons the skilled artisan will appreciate, an overhang is preferred. More preferably the tags, when ligated together, regenerate the recognition sequence for the punctuating restriction endonuclease allowing the recognition of discrete cDNA-derived sequences owing to their separation by the punctuating sequence.

"A tag sequence" as used herein, means DNA sequence comprising at least one tag sequence. An array of tags includes a number of tags, having one or more sequences. The tag sequence can be included in linear oligonucleotide, in a vector or the like.

"A cDNA tag library" as used herein, means a cDNA library prepared in a vector comprising (1) ligated fragment of a 5' adapter cleaved with a 5' cloning restriction endonuclease, (2) ligated fragment of 3' adapter cleaved with a 3' cloning restriction endonuclease, and (3) a tag. A cDNA tag library is cloned into a cloning vector and can be amplified in a host cell.

"An array of tags" as used herein, means tags ligated with their cohesive ends or blunt ends as to form double-stranded DNA sequence. The array of tags is also referred to as "a concatemer", which means concatenated tags. The array of tags can be included in a vector. Preferably, an array of tags comprises cDNA sequences interspersed by recognition sequences for a punctuating restriction endonuclease. The ligated arrays of tags comprise approximately at least 10 tags, preferably at least 30 tags, more preferably at least 40 tags and less than 70 tags, more preferably less than 60 tags, most preferably less than about 51 tags. More preferably, an array of tags begins with and ends with a recognition sequence for the punctuating restriction endonuclease. Most preferably, the recognition sequence for the punctuating restriction endonuclease is located between each tag.

"A punctuation sequence" as used herein, means a sequence formed by ligating two ends digested with a punctuating restriction endonuclease as detected in a sequence of an array of tags which punctuates DNA nucleotide sequences.

"A clamp" as used herein, means a base-pair derived from the recognition sequence from a punctuating restriction endonuclease which remains attached to the cDNA-derived sequence when a tag is generated by digestion with the punctuating restriction endonuclease. The base composition of a clamp preferably consists of guanine (G) and cytosine (C), and is referred to as "a GC-clamp", which means a clamp consisting of G and C. The function of a GC-clamp is to enhance thermal stability of a tag by increasing the number of hydrogen bonds which hold the anti-parallel strands of a tag together after digestion with the punctuating restriction endonuclease.

"GC rich" as used herein, means a sequence in which the percentage of bases which are G or C is more than 40%, preferably more than 50%.

"Correspond," as used herein, means that at least a portion of one nucleic acid molecule is either complementary to or identical to a second nucleic acid molecule. Thus, a cDNA molecule may correspond to the mRNA molecule where the mRNA molecule was used as a template for reverse transcription to produce the cDNA molecule. Similarly, a genomic sequence of a gene may correspond to a cDNA sequence where portions of the genomic sequence are complementary or identical to the cDNA sequence.

"Hybridize" as used herein, means the formation of a base-paired interaction between nucleotide polymers. The presence of base pairing implies that a fraction of the nucleotides (e.g., at least 80% of a group of adjacent bases in a nucleotide) in each of two nucleotide sequences are complementary to the other according to the commonly accepted base pairing rules. The exact fraction of the nucleotides which must be complementary in order to obtain stable hybridization will vary with a number of factors, including nucleotide sequence, salt concentration of the solution, temperature, and pH.

"Stringent conditions" as used herein, means conditions in which stable hybridization of complementary oligonucleotides is maintained, but mismatches are not (Sambrook et al., *Molecular Cloning* (1989), see for example, 11.46; RNA hybrids and 9.51, RNA:DNA hybrids. Preferably, stringent condition means incubation at 25–65° C. in 1–6×SSC. More preferably, stringent condition means incubation at 42–65° C. in 4–6×SSC.

"A probe" as used herein, means an oligonucleotide or a vector containing a tag or tag-derived (that is, derived from all or part of a tag) sequence, used to hybridize to a pool of RNA or DNA and detect nucleic acids of interest by any of a variety of methods known to those skilled in the art.

"A vector" as used herein, means an agent into which DNA of this invention can be inserted by ligation into the DNA of the agent allowing replication of both the insert and agent in a suitable host cell. Examples of classes of vectors can be plasmids, cosmids, and viruses (e.g., bacteriophage). A cloning vector is used for cloning DNA sequences comprising a tag sequence to form a cDNA tag library. More preferably, as a cloning vector, pUC18 and pUC19 are used. Preferably, the endogenous recognition sites for a punctuating restriction endonuclease within the cloning vector have been destroyed by site-directed mutagenesis. A sequencing vector is used to clone tags or arrays of tags in preparation for DNA sequence analysis. As a sequencing vector, pUC18 and pUC19 are preferred.

This invention provides a method of obtaining a tag comprising the steps of:
(a) providing a double-stranded cDNA,
(b) cleaving the double-stranded cDNA with a punctuating restriction endonuclease providing a cDNA fragment,
(c) ligating to the cDNA fragment a 5' adapter which is blunt or preferably contains a single-stranded overhang compatible with the punctuating restriction endonuclease. Such ligation produces a first cDNA construct in which the recognition sequence for the punctuating restriction endonuclease is regenerated. The 5' adapter also contains a recognition sequence for a type IIs restriction endonuclease which allows DNA cleavage at a site in the cDNA fragment distant from the recognition sequence for the type IIs restriction endonuclease,
(d) cleaving the first cDNA construct with the type IIs restriction endonuclease providing a second cDNA construct, preferably this construct has 10–14 basepairs of cDNA-derived sequence and is flanked at its 3' end by a random single-stranded overhang and at its 5' end by the recognition sequence of the punctuating enzyme as well as additional sequence derived from the 5' adapter,
(e) ligating to the second cDNA construct a 3' adapter, where the adapter has overhangs, it contains degenerate single-stranded overhangs compatible with all possible overhangs present in the first cDNA construct. The 3' adapter also contains a recognition sequence for the punctuating restriction endonculease which is preferably located immediately proximal to the degenerate single-stranded end if used. Hence, ligation of the 3' adapter to the first cDNA construct generates a cDNA construct in which a cDNA-derived sequence of 10–14 bases is flanked at both ends by the recognition sequence for the punctuating restriction endonuclease, as well as additional sequence located at either end, providing a third cDNA construct,
(f) digesting the third cDNA construct with a 5' and 3' cloning restriction endonuclease to provide a fourth cDNA construct which is ligated into a like digested cloning vector ("like digested" means digested to provide ends which can be ligated to the other ends of the vector or construct) and amplified by growth in a suitable host to form a tag library, and
(g) optionally isolating vector DNA from the tag library and digesting the DNA with the punctuating restriction endonuclease to release the tag from the vector, and (h) determining the nucleotide sequences of the tag(s).

Preferably, this invention provides a method of obtaining an array of tags, comprising the steps of:
(a) providing double-stranded cDNA from an mRNA using a biotinylated oligo dT primer,
(b) cleaving the double-stranded cDNA with a punctuating restriction endonuclease which cleaves within the cDNA providing a population of a cDNA fragment,
(c) ligating to the cDNA fragment a 5' adapter comprising,
  i) a single-stranded end compatible with ends produced by cleavage with the punctuating endonuclease;
  ii) a recognition sequence for a type IIs restriction endonuclease located 5' to the single-stranded end;
  iii) a recognition sequence for a 5' cloning restriction endonuclease located 5' to a recognition sequence for the type IIs restriction endonuclease, providing a first cDNA construct,
(d) isolating the first cDNA construct by affinity capture (sucha as chromatography, loose beads, magnetic media or the like) on preferably solid phase streptavidin,
(e) cleaving the first cDNA construct with the type IIs restriction endonuclease from the solid phase and/or streptavidin providing a second cDNA construct,
(f) ligating to the second cDNA construct a 3' adapter comprising,
  i) a degenerate single-stranded end compatible with any ends produced by the type IIs restriction endonuclease;
  ii) a recognition sequence for the punctuating endonuclease located 3' to the degenerate end;
  iii) a recognition sequence for a 3' cloning restriction endonuclease located 3' to a recognition sequence for the punctuating endonuclease, providing a third cDNA construct,
(g) digesting the third cDNA construct with the third and 3' cloning restriction endonucleases providing a fourth cDNA construct;
(h) inserting the fourth cDNA construct into a cloning vector digested with the third and 3' cloning restriction endonucleases,
(i) replicating the vector DNA in a suitable host strain,
(j) isolating the vector DNA,
(k) digesting the vector DNA with the punctuating endonuclease providing a tag comprising cDNA sequences and GC rich clamps,
(l) ligating the tags providing arrays of tags comprising at least 10 tags and GC rich clamps,
(m) optionally inserting the arrays of tags into a sequencing vector,
(n) optionally determining the nucleotide sequences of the arrays of tags.

Double-stranded cDNA is prepared from the target mRNA pool by standard methods using oligo-dT primer. The oligo-dT primer is preferably biotinylated. Preferably, the double-stranded cDNA is treated with methylase or other protection means for a 5'-cloning restriction endonuclease and/or a 3'-cloning restriction endonuclease to protect any internal endonuclease recognition sites.

Double-stranded cDNA is cleaved with a punctuating endonuclease under any known conditions providing a cDNA fragment. The punctuating restriction endonuclease cleaves within the cDNA fragment.

A synthetic, double-stranded adapter molecule with a single-stranded overhang compatible with the punctuating restriction endonuclease, is ligated to the cDNA fragment. The 3'-most cDNA fragment is then isolated by affinity capture, preferably such as biotin and streptavidin, on solid phase which is extensively washed to remove free 5' adapter providing a first cDNA construct. The 5' adapter introduces a recognition sequence for a type IIs restriction endonuclease, preferably BsgI; immediately 5' to the ligated cDNA fragment. Preferably, the 5' adapter contains a recognition sequence for a 5' cloning restriction endonuclease, at its 5' terminus to facilitate later cloning.

Cleavage of the adapter-ligated, preferably solid-phase bound cDNA fragment with the type IIs restriction endonuclease releases into the solution phase a linear DNA fragment consisting of the adapter itself and additional nucleotides of unknown cDNA sequence separated from the adapter by the punctuation sequence providing a second cDNA construct.

A second cDNA construct is then ligated to a 3' adapter molecule which, if an overhang, such as a two base overhang, is used, would have a 16-fold degenerate overhang at the 5' end of the 3' adapter which renders it compatible with all possible cDNA overhang sequences released by the type IIs restriction endonuclease, providing a third cDNA construct. Preferably, the 3' adapter contains a recognition sequence for a 3'-cloning restriction endonuclease. This adapter introduces a recognition sequence for the punctuating restriction endonuclease to the 3' end of the second cDNA construct, such that the construct contains a cDNA-derived "tag" sequence flanked at both ends by punctuation sequence produced by a 5' and a 3' adapter.

The third cDNA construct is digested with the punctuating endonuclease under conditions known to person skilled in the art, thus providing a tag. Digestion with the punctuating endonuclease provides a tag which comprises cDNA sequences with a recognition sequence for a punctuating endonuclease at its ends. The resulting tag can be inserted for example, into a cloning vector to amplify in microorganisms. After amplification, the tag sequence is determined by any known method.

Alternatively, instead of digesting a third cDNA construct with the punctuating restriction endonuclease, the resulting third cDNA construct is digested with the 5' and 3'-cloning restriction endonucleases providing a fourth cDNA construct. The third cDNA construct can be digested initially with either of 5' or 3' restriction endonuclease or digested with both restriction endonucleases simultaneously. In this case the fourth cDNA construct is isolated by any known method including gel electrophoresis or the like, to resolve it from dimers of the adapters which are also formed in the ligation reaction. These manipulations result in a 5' and 3'-cloning restriction endonuclease-tailed DNA fragment containing a cDNA tag flanked at both ends by the punctuation sequence. The resulting fourth cDNA construct is isolated from the isolation means, or resolving means by known methods, such as eluting from a gel and recovery by ethanol precipitation.

Before inserting the fourth cDNA construct into a cloning vector (digested with the 5' and 3'-clonong restriction endonuclease), it is preferred that any endogenous punctuating endonuclease restriction sites in the vector have been removed by site-directed mutagenesis. As a cloning vector, pUC18 or pUC19 are preferably used. The cloning vector is digested with a 5' and 3'-cloning restriction endonuclease and a fourth cDNA construct is inserted into the cloning vector.

The cloning vectors are replicated using any method known in the art. Preferably, the cloning vector comprising cDNA construct is amplified in a host cell such as, but not limited to, E. coli by first transforming E. coli with the vector comprising cDNA construct, growing the transformed cells, and isolating the cloning vector from cell culture.

Preferably, cultured host cells are collected by centrifugation and then plasmid DNA is prepared from the precipitate using any known procedures to isolate the vector DNA.

The plasmid DNA is digested with the punctuating restriction endonuclease to release the tags. Each tag is a DNA fragment consisting of a 10–14 base-pair sequence derived from the cDNA. The resulting tag is flanked at both ends, preferably by compatible single-stranded overhangs, which are derived from recognition sequence for a punctuating endonuclease. When the punctuating endonuclease is MspI, tags have GC single-stranded 3' overhang and CG single-stranded 5' overhangs. A GC clamp prevents the melting of tags at ambient temperatures and attendant bias against AT-rich sequences. The tag fragments are isolated away from the plasmid backbone by acrylamide gel electrophoresis, eluted from the gel and recovered by ethanol precipitation in preparation.

Tags are ligated together via their compatible ends to form arrays of tags. The arrays of tags are isolated by agarose gel electrophoresis.

Arrays of tags are inserted into a sequencing vector in preparation for DNA sequence analysis. As a sequencing vector, any vector is useful. Preferably, pGEM®(Promega Corp., Madison, Wis.), pBluescript® (Stratagene, La Jolla, Calif.), pUC18 or pUC19 are used. More preferably, pUC19 can be used. Each array consists of preferably, 10–14-base pair tag sequences separated from each other and from the plasmid backbone by the defined 4-base punctuation sequence.

Any known procedures are used for sequencing analysis to determine the nucleotide sequences of the tag or the arrays of tags.

This method allows mRNAs with a number of copies to be detected in a given cell population. By comparing gene transcription profiles among cells, this method can be used to identify individual genes whose transcription is associated with a pathological phenotype.

Using high throughput DNA sequencing, the method of this invention also permits the generation of a global gene transcription profile. Thus, this invention provides a simple and rapid method of obtaining sufficient data to use in an information system known to those of skill in the art to obtain a global gene transcription profile and identify genes of interest.

Accordingly, this invention can be used to identify differential gene transcription patterns among two or more cells or tissues. Thus, using the methods of this invention one can identify a gene or genes that are transcribed in any given cell type, tissue, or target organism at a different level from that in another cell type, tissue, or target organism.

The methods of this invention can be used to identify differential gene transcription patterns at different stages of development in the same cell-type or tissue-type, and to identify changes in gene transcription patterns in diseased or abnormal cells. Further, this invention can be used to detect changes in gene transcription patterns due to changes in environmental conditions or to treatment with drugs. To do so, patterns of gene transcription are compared using double-stranded cDNA obtained from different mRNA populations of interest.

This invention also provides a method of identifying patterns of gene transcription, comprising steps of:

(a) providing tags from sources of interest according to this invention, and (b) identifying patterns of gene transcription.

Tags are prepared from an mRNA population of interest according to this invention and their sequences are determined using conventional procedures.

Sequences of resulting tags are compared to known sequence databases to identify patterns of gene transcription.

This invention also provides a method of detecting a difference in gene transcription between two or more mRNA populations, comprising steps of:
- (a) identifying patterns of gene transcription from a first mRNA population according to this invention,
- (b) identifying patterns of gene transcription from a second mRNA population according to this invention, and
- (c) comparing the patterns of gene transcription from (a) and (b).

Preferably, the first mRNA population is obtained from a normal cell or tissue. Patterns of gene transcription from a first mRNA population are then identified. Preferably, the second mRNA population and/or any additional mRNA population is obtained from a target organism having a disease or disorder, cells or tissues at different developmental stages, different tissues or organs of the same target organism or different target organisms and patterns of gene transcription are identified.

The patterns obtained from the first and second mRNA populations are compared and the difference is observed. In addition, patterns from other mRNA populations can be compared to those initially derived. This method is also useful in identifying genes modulated by development, disorders, drugs, stress, disease or the like.

This invention also provides a method of determining the relative frequency of a particular gene's transcription compared to other genes transcribed into an mRNA population comprising the steps of:
- (a) providing an array of tags of interest,
- (b) sequencing the array of tags, and
- (c) determining relative frequency of any or all tags.

An array of tags is prepared based on this invention from cDNA library from an mRNA population.

The array of tags can be sequenced by using any known methods, such as sequencing by hybridization method, (see for example U.S. Pat. No. 5,202,231, hereby incorporated by reference).

Once sequencing of tags is accomplished, determining the frequency of tags is done by any method available. For example, this can be done manually or using a suitable algorithm and/or a computer searchable database.

This invention also provides a method of screening for a disease, a disorder, or the like stress as defined above, including the effects of a drug on a cell or tissue comprising the steps of:
- (a) identifying patterns of gene transcription in the normal cell according to this invention,
- (b) identifying patterns of gene transcription in the presence of a stress or the like according to this invention,
- (c) comparing the patterns of gene transcription from (a) and (b).

For example, the differences in the patterns of gene transcription between cells cultured with the drug and those without the drug is compared to determine whether the drug changes the gene transcription profile. This method yields information on (1) markers useful in diagnosis of disease or other stress as defined above, such as by blood test, the like, and/or (2) determining target enzymes or proteins for treatment and thus providing an aid in drug design or development.

This invention also provides a method of detecting the presence of a disease, or other stress as defined above in a target organism comprising the steps of:
- (a) providing the tag sequence of a gene that is differentially expressed (either expressed more abundantly-increased expression, or expressed less abundantly-decreased expression, that is the disease or other stress as defined above modulates expression in some way) in a normal cell or tissue according to this invention,
- (b) hybridizing a cDNA library obtained from a first target organism with the tag,
- (c) hybridizing a cDNA library obtained from a second normal or diseased (or effected by other stress as defined above) target organism with the tag sequence, and
- (d) comparing the level of transcription of the gene in the first target organism with the level of transcription of the gene in the second target.

Any known methods are employed to detect the presence of a disease or other stress as defined above in the first target organism to compare the level of transcription of the gene in the first target organism with the level of transcription of the gene in the second target organism.

This invention also provides a method of isolating a gene, comprising the steps of:
- (a) providing a probe comprising a tag sequence of interest according to this invention,
- (b) probing cDNA library of interest, and
- (c) isolating a gene.

Any tag of interest can be used to provide a probe comprising a tag sequence of interest. This probe can be used to find a new gene, detect a gene in a cell, or detect a mutation. A probe comprising a tag sequence is prepared using synthetic oligonucleotide or a vector comprising a tag sequence. A probe is preferably labeled for detection by radioisotope, fluorescence and the like, or for isolation such as by biotin, streptavidin or the like.

The nucleotide sequence of a tag is compared with known nucleotide sequences to determine which gene to isolate. Known nucleotide sequences can be obtained from any source using sequence databases, such as GenBank, etc. This invention also provides a kit for obtaining a tag or an array of tags comprising:
- (a) a 5' adapter,
- (b) a 3' adapter
- (c) appropriate vectors, including cloning and/or sequencing vectors, and
- (d) appropriate restriction endonucleases, as disclosed herein.

The kit can further include reaction buffer and/or cDNA library and other such components.

Hence, this invention provides a rapid and accurate means to quantitatively analyze the gene transcription profile of interest and to compare profiles between different sources for a host of reasons.

The method also assists in new gene discovery because the 10–14-bp tag sequences generated by this invention can serve as hybridization probes to facilitate the isolation of interesting tagged genes whose function is not yet known. Isolation of genes using such tags is well understood in the art.

EXAMPLES

To assist in understanding the present invention, the following Examples are included which describes the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

Example 1

Preparation of a cDNA Tag TAG Library (1)

(a) cDNA Synthesis

Ten µg of polyA+ RNA from normal adult human lung (Clontech, Inc., Palo Alto, Calif.) was primed with 5' biotinylated oligo dT(25) and copied into cDNA (Superscript II® cDNA synthesis kit from GIBCO Life Technologies, Gaithersburg, Md.). The cDNA was phenol/chloroform extracted and ethanol precipitated. The pellet was dissolved in 50 µl of buffer (1×NEB buffer #2 from New England Biolabs (NEB), Tozer, Mass.) containing 200 units of MspI (NEB) and digested for 1 hour at 37° C. followed by 20 minutes at 65° C. to inactivate the enzyme.

The reaction mix was brought to 800 µl in magnetic bead binding buffer, added to 600 µl of streptavidin magnetic beads (Dynal, Inc., Lake Success, N.Y.), which were previously washed and from which all wash buffer was removed. The total volume of this solution was 800 µl. This solution was incubated overnight at room temperature with gentle rotation. Beads were washed 5 times using a magnetic capture device with 10 mM Tris-HCl, pH 7.6 followed by a final wash in 0.5×T4 ligase buffer (GIBCO).

(b) Adapter Ligation and Library Generation

Oligonucleotide adapters (5' adapter) were created by mixing synthetic oligos, heating them to 95° C., and allowing them to cool slowly to room temperature. Sense strand of this oligonucleotide adapter has a sequence of SEQ ID NO. 5 and antisense strand of this oligonucleotide adapter has a sequence of SEQ ID NO. 6. 7.6 µg of 5' adapter DNA was added to the magnetic bead mix in a volume of 100 µl of 0.5×T4 ligase buffer containing 50 units of T4 ligase (GIBCO) and incubated 2 hours at room temperature. Beads were then washed 5 times in 10 ml of 10 mM Tris-HCl, pH 7.6. The beads were resuspended in 4 aliquots of 500 µl each and incubated at 65° C. for 20 minutes. The beads were then washed 5 times in 10 ml of 10 mM Tris-HCl, pH 7.6. Beads were then resuspended in 360 µl of NEB buffer 4 containing 80 µM SAM (5-adenosylmethionine).

The beads were divided into 4 aliquots of 90 ul each and 40 units BsgI (NEB) was added to each aliquot. The beads were then incubated at 37° C. for 1.5 hours. The tag-containing supernatants were pooled. This solution was extracted with phenol/chloroform and ethanol precipitated with 20 µg of mussel glycogen carrier.

A second, 16-fold degenerate adapter (3' adapter) molecule was prepared by annealing synthetic oligos. Sense strand of this 16-fold degenerate adapter has a sequence of SEQ ID NO. 7 and antisense strand of this 16-fold degenerate adapter has a sequence of SEQ ID NO. 8.

7.9 µg of 3' adapter was added to the tag DNA pellet in a total volume of 30 µl of ligase buffer containing 10 units T4 DNA ligase and incubated for 2 hours at room temperature. The ligase mix was heat inactivated by incubation at 65° C. for 20 minutes.

The reaction mix was loaded on a 15% TAE (1×TAE; 40 mM Tris-Acetate, 1 mM EDTA) acrylamide gel to resolve the 68 bp fragments containing cDNA tags from multimers of the adapter. cDNA tag fragments were excised from the ethidium bromide(EtBr)-stained gel, eluted overnight in 500 µl of TE (10 mM Tris, 1 mM EDTA), and ethanol precipitated with 20 µg mussel glycogen carrier. Tag DNA was quantified by spectrophotometer and ligated overnight at 16° C. into the dephosphorylated EcoR1 and NotI sites of a vector of pUC19 (Bayou Biolabs, Harahan, La.) in which endogenous MspI sites were destroyed by site-directed mutagenesis at a 3:1 insert: vector ratio. The ligation mix was transformed into competent cells (XL-10 Gold® from Stratagene, La Jolla, Calif.) which were grown in 5 L of LB medium containing 100 µg/ml ampicillin.

(c) Tag Isolation and Concatemer Formation

Transformed bacteria were recovered by centrifugation and plasmid DNA was isolated (Mega Plasmid Prep Kit from Qiagen, Inc., Valencia, Calif.). One mg of plasmid DNA was digested with 5000 units MspI in a total volume of 1 ml at 20° C., for 1 hour. This reaction was loaded into 12 lanes of a 15% TAE acrylamide gel. Tag fragments were excised from the EtBr-stained gel, eluted overnight in approximately 1 ml of TE and ethanol precipitated with 20 µkg mussel glycogen carrier.

Purified tags were resuspended in 20 µl ligase buffer containing 10 units T4 ligase, and incubated at room temperature for 1.5 hours. This was followed by an additional 20 minute incubation with 5 units of Klenow fragment and 2 mM dNTPs. The reaction was then loaded onto a 1% TAE agarose gel containing EtBr and electrophoresed. Nucleic acids of 600–1200 bp in length were isolated from the gel, ethanol precipitated and resuspended in 10 µl of ligation buffer containing 50 ng SmaI-cut, alkaline phosphatase-treated pUC19, and 5 units of T4 ligase, and incubated overnight at 16° C. One µl of the ligation mix was transformed into 100 µl of competent cells (XL-10 Gold® from Stratagene). The reaction mix was plated on LB-Amp plates with IPTG-XgaI and individual white colonies were picked for DNA sequence analysis.

(d) DNA Sequencing

Arrays of ~600 bp or greater were purified by agarose gel electrophoresis and cloned into pUC19. Sequencing-grade plasmid templates from about 700 independent colonies were prepared in 96-well plates (Qiagen BioRobot 9600). Templates were subjected to cycle sequencing (PE-ABI BigDye® terminator chemistry from PE Applied Biosystems, Forster City, Calif.) with the M13 reverse primer. Reactions were run on automated sequencers (ABI 377 automated sequencers). Extracted data were ported to a SyBase database and subjected to automated DNA sequence analysis (BioLIMS® sequencing Analysis, ver. 3.1.3 system from PE-ABD).

A frequency distribution of tags was generated and searched against a database to generate a small transcription profile. The profile contained 14,496 unambiguous tag sequences representing 2560 independent genes. The number of identifiable tags in each array ranged from 2 to 63 with an average of 32 tags per array.

Most of the abundant tags corresponding to identifiable genes in this profile have been previously described as being

Example 2

Preparation of cDNA Tag Library (2)

(a) cDNA Sythesis

Ten µg of polyA+ RNA from normal adult human lung (Clontech, Inc.) was primed with 5' biotinylated oligo dT(25) and copied into cDNA (Superscript II® cDNA synthesis kit from GIBCO). The cDNA was ethanol precipitated. The pellet was dissolved in 80 µl of EcoRI Methylation Buffer (NEB) containing 80 µM S-adenosylmethionine (SAM) (NEB) and 320 units of EcoRI Methylase (NEB) and incubated for 1 hour at 37° C. followed by 15 minutes at 65° C. to inactivate the enzyme. The reaction mix was brought to 800 µl with water and spun through a spin filter (Microcon 50, Amicon Inc., Beverly, Mass.) until 60 ul was retained.

MspI digestion was performed in 80 µl of buffer (1×NEB buffer #2) containing 10 mM MgCl$_2$ and 400 units of MspI (NEB) and digested for 2 hours at 37° C. followed by 20 minutes at 65° C. to inactivate the enzyme. The reaction mix was brought to 880 µl with water and spun through a spin filter (Microcon 30, Amicon) until about 60 µl was retained.

(b) Adapter Ligation and Library Generation

Oligonucleotide adapters (5' adapter) were created by mixing synthetic oligos, heating them to 95° C., and allowing them to cool slowly to room temperature. Sense strand of this oligonucleotide adapter has a sequence of SEQ ID NO. 1 and antisense strand of this oligonucleotide adapter has a sequence of SEQ ID NO. 2.

54 µg of 5' adapter DNA was added to the MspI-digested cDNA in a volume of 150 µl of 1×T4 DNA ligase buffer containing 37.5 units of T4 DNA ligase (GIBCO) and incubated 2 hours at room temperature. 150 µl of 10 mM Tris, 1 mM EDTA, 1 M NaCl was added to the reaction followed by 20 minutes at 65° C. to inactivate the enzyme. The 300 µl reaction mix was added to 900 µl of streptavidin magnetic beads (Dynal, Inc.), which were previously washed and from which all wash buffer had been removed. This solution was incubated overnight at room temperature with gentle rotation. Beads were washed 5 times in 10 ml each of 10 mM Tris-HCl, pH 7.6, using a magnetic capture device. The beads were suspended in 2 ml 5 mM Tris-pH 7.6 with 250 mM NaCl and incubated at 65° C. for 20 minutes to further inactivate the enzyme. The beads were then washed 5 times in 10 ml each of 10 mM Tris-HCl, pH 7.6. Beads were then washed once with 1 ml of 1×NEB buffer 4 containing 80 µM SAM.

The beads were suspended in 200 µl of 1×NEB buffer 4 containing 80 µM SAM and 100 units of BsgI (NEB). The beads were incubated at 37° C. for 2 hours with gentle rotation. The tag-containing supernatant was saved and the beads were washed two times with 200 µl 10 mM Tris-pH7.6. The washes and supernatant were pooled and 30 µl 5M NaCl was added. The pooled supernatant and washes were then incubated at 65° C. for 20 minutes to inactivate the enzyme. This solution was spun over a Microcon 10 (Amicon) spin filter until the volume was about 30 µl.

A second, 16-fold degenerate adapter molecule (3' adapter) was prepared by annealing synthetic oligos. Sense strand of 16-fold degenerate adapter has a sequence of SEQ ID NO. 3 and antisense strand of 16-fold degenerate adapter has a sequence of SEQ ID NO. 4. 3' adapter has 1 or more biotinylated phosphoamidites incorporated on the 3' end of the oligo during oligo synthesis.

10.8 µg of 3' adapter was added to the tag DNA in a total volume of 45 µl of T4 DNA ligase buffer containing 10 units T4 DNA ligase and incubated for 2 hours at room temperature. The ligase mix was heat inactivated by incubation at 65° C. for 20 minutes.

The tag DNA was digested with NotI in a total volume of 250 µl 1×React 3 buffer (Gibco) containing 1×bovine serum albumin (BSA) and 625 units of NotI (Gibco) and incubated at 37° C. overnight.

The NotI digestion reaction was digested with EcoRI in 500 µl of 1×React 3 buffer with 1250 units of EcoRI and incubated at 37° C. for 2 hours followed by addition of 5 µl 0.5M EDTA and 90 µl 5M NaCl. The reaction was heat inactivated by incubation at 65° C. for 20 minutes.

The 500 µl reaction mix was added to 300 µl of streptavidin magnetic beads (Dynal, Inc.), which were previously washed and from which all wash buffer had been removed. This solution was incubated overnight at room temperature with gentle rotation.

The supernatant from binding was collected and spun on a spin filter (Microcon 10, Amicon) until the retained volume was about 30 µl.

The concentrated reaction mix was loaded on a 10% TAE acrylamide gel to resolve the 93 bp fragments containing cDNA tags from multimers of the adapter. cDNA tag fragments were excised from the EtBr-stained gel, eluted overnight in 300 µl of TE, and ethanol precipitated with 15 µg GLYCOBLUE (Ambion Inc., Austin, Tex.) carrier. Tag DNA was quantified by spectrophotometer and ligated overnight at 16° C. into the dephosphorylated EcoR1 and NotI sites of a vector of pUC19 in which endogenous MspI sites were destroyed by site-directed mutagenesis at a 1:4 insert:vector ratio. The ligation mix was transformed into competent cells (XL-10 Gold® from Stratagene, La Jolla, Calif.) which were grown in 2 L of LB medium containing 100 µg/ml ampicillin.

(c) Tag Isolation and Concatemer Formation

Transformed bacteria were recovered by centrifugation and plasmid DNA was isolated (Mega Plasmid Prep Kit from Qiagen, Inc.). One mg of plasmid DNA was digested with 5000 units MspI in a total volume of 1 ml at 20° C., for 1 hour. This reaction was loaded into 12 lanes of a 15% TAE acrylamide gel. Tag fragments were excised from the EtBr-stained gel, eluted overnight in approximately 1 ml of TE and ethanol precipitated with 15 µg GLYCOBLUE (Ambion) carrier.

Purified tags were resuspended in 20 µl ligase buffer containing 10 units T4 DNA ligase, and incubated at room temperature for 1.5 hours. This was followed by an additional 20 minute incubation with 5 units of Klenow fragment and 2 mM dNTPs. The reaction was then loaded onto a 1% TAE agarose gel containing EtBr and electrophoresed.

Nucleic acids of 600–1200 bp in length were isolated from the gel, ethanol precipitated and resuspended in 10 µl of ligation buffer containing 50 ng SmaI-cut, alkaline phosphatase-treated pUC19, and 5 units of T4 DNA ligase, and incubated overnight at 16° C. One µl of the ligation mix was transformed into 100 µl of competent cells (XL-10 Gold® from Stratagene). The reaction mix was plated on LB-Amp plates with Isopropyl-1-thio-B-D-galactopyranoside (IPTG, Stratagene) and 5-bromo-4-chloro-3-indolyl-B-D-galactopyranoside (XgaI, Stratagene) and individual white colonies were picked for DNA sequence analysis.

(d) DNA Sequencing

Arrays of ~600 bp or greater were purified by agarose gel electrophoresis and cloned into pUC19. Sequencing-grade plasmid templates were prepared in 96-well plates (Qiagen BioRobot 9600). Templates were subjected to cycle sequencing (PE-ABI BigDye® terminator chemistry from PE Applied Biosystems, Forster City, Calif.) with the M13 reverse primer. Reactions were run on automated sequencers (ABI 377 automated sequencers). Extracted data were ported to a SyBase database and subjected to automated DNA sequence analysis (BioLIMS® Sequencing Analysis, ver. 3.1.3 system from PE-ABD).

Example 3

Comparision of a cDNA Tag Library to a Standard cDNA Library

To characterize a tag as corresponding to a gene, we produced a standard oligo dT-primed cDNA library of about 1,000,000, primary plaques in lambda-gt10 (Huynh, T. V. et al., DNA Cloning: A Practical Approach, D. Glover, Ed. (IRL Press, Oxford) (1984)).

A series of replicate nitrocellulose filter lifts were prepared from large plates containing ~18,000 plaques. These filters were probed with end-labeled oligonucleotides corresponding to identified tag sequences. The frequencies of probe hybridization match well with the corresponding tag frequencies in the profile. Clones hybridizing to the tag were isolated and subjected to DNA sequence analysis.

This analysis confirmed the identity of the tagged gene and its relative expressed abundance compared to a cDNA library.

Example 4

Determination of PCR Amplification Based Methods Errors on Quantitation

Two pairs of complementary oligonucleotides corresponding to synthetic amplicons were synthesized and annealed. Each amplicon contains a single di-tag of 18-bases in length flanked by anchoring enzyme sequences (CATG) and PCR priming sites exactly as described by Velculescu et al. Science, 270: 484 (1995). One of the tags in each amplicon is an identical 9-base arbitrary sequence (CTGTTAGTA). This common tag sequence was paired with either an AT-rich non-palindromic "tag" sequence (TATAATAAA for amplicon 1) or a GC rich palindromic sequence (CCCGATCGG for amplicon 2) to form artificial di-tags. The entire double-stranded synthetic amplicon terminates in single-stranded ends compatible with BamHI and HindIII digested vectors to facilitate cloning.

These artificial amplicons were ligated into a plasmid vector, and a precisely equivalent concentration of plasmid DNA was prepared from each. This plasmid DNA was diluted and subjected to either 15 or 20 cycles of amplification using 6-FAM (6-carboxyfluorescein) end-labeled primers and amplification conditions described in Velculescu et al., Science, 270: 484 (1995).

The intensity of the bands derived from the corresponding PCR products was not identical. After 15 cycles of amplification, there was no visible PCR product derived from amplicon 2 while the band derived from amplicon 1 was clearly evident. When the cycle number was increased to 20, both PCR products were visible, but peak area analysis (PE Biosystems Prism 377 Genescan™ software from PE, Santa Fe, N. Mex.) demonstrated that the quantity of product derived from amplicon 1 was more than 5 times that of amplicon 2, despite the fact that there was no difference in starting template concentration or PCR primers. The clear implication is that the amount of PCR product produced after amplification can be dramatically influenced by the sequence of any tag within it.

All references cited herein are hereby incorporated by reference, whether specifically stating that they are incorporated by reference or not, as if fully set forth for the matter they contain.

I claim:

1. A method of obtaining a set of tags from a source of interest comprising the steps of:
   (a) providing a double-stranded cDNA, having a poly A or a poly T tail,
   (b) cleaving said double-stranded cDNA with a punctuating restriction endonuclease providing a cDNA fragment,
   (c) ligating to said cDNA fragment a 5' adapter comprising a recognition sequence for a type IIs restriction endonuclease which allows DNA cleavage at a site in the cDNA fragment distant from the recognition sequence for a type IIs restriction endonuclease providing a first cDNA construct,
   (d) cleaving said first cDNA construct with said type IIs restriction endonuclease providing a second cDNA construct,
   (e) ligating to said second cDNA construct a 3' adapter, thereby producing a recognition sequence for a punctuating endonuclease located 3' adjacent to said second cDNA construct, providing a third cDNA construct,
   (f) digesting said third cDNA construct with said punctuating restriction endonuclease providing a set of tags comprising cDNA sequences, and
   (g) determining the nucleotide sequences of said set of tags.

2. The method of claim 1, wherein the punctuating restriction endonuclease is MspI and the type IIs restriction endonuclease is BsgI.

3. A method of claim 1 further comprising the step of ligating said set of tags providing an array of tags.

4. The method of claim 3 further comprising the step of introducing said array of tags into a vector.

5. A method of obtaining an array of tags, comprising the steps of:
   (a) providing double-stranded cDNA from an mRNA using a biotinylated oligo dT primer,
   (b) cleaving within said double-stranded cDNA with a punctuating restriction endonuclease providing a population of a cDNA fragments,
   (c) ligating to said cDNA fragment a 5' adapter comprising,
      i) a single-stranded end compatible with ends produced by cleavage with said punctuating restriction endonuclease;
      ii) a recognition sequence for a type IIs restriction endonuclease located 5' to said single-stranded end;
      iii) a recognition sequence for a 5'-cloning restriction endonuclease located 5' to a recognition sequence for said type IIs restriction endonuclease, providing a first cDNA construct,
   (d) isolating said first cDNA construct by affinity capture on solid phase streptavidin,
   (e) cleaving said first cDNA construct with said type IIs restriction endonuclease providing a second cDNA construct,
   (f) ligating to said second cDNA construct a 3' adapter comprising,
      i) a degenerate single-stranded end compatible with ends produced by said type IIs restriction endonuclease;
      ii) a recognition sequence for said punctuating restriction endonuclease located 3' to said degenerate end;
      iii) a recognition sequence for a 3'-cloning restriction endonuclease located 3' to a recognition sequence for said punctuating restriction endonuclease, providing a third cDNA construct,
   (g) digesting said third cDNA construct with said 5' and 3'-cloning restriction endonucleases providing a fourth cDNA construct;
   (h) inserting said fourth cDNA construct into a cloning vector digested with said 5' and 3'-cloning restriction endonucleases,
   (i) replicating said vector DNA in a suitable host strain,
   (j) isolating said vector DNA,
   (k) digesting said vector DNA with said punctuating restriction endonuclease providing a set of tags comprising cDNA sequences and a GC clamp,
   (l) ligating said set of tags providing arrays of tags comprising at least 10 tags and GC rich clamps,
   (m) optionally inserting said arrays of tags into a sequence vector, and
   (n) optionally determining the nucleotide sequences of the arrays of tags.

6. The method of claim 5, wherein the punctuating restriction endonuclease is MspI and the type IIs restriction endonuclease is BsgI.

7. The method of claim 5, wherein the 5' cloning restriction endonuclease is EcoRI and the 3'-cloning restriction endonuclease is NotI.

8. A method of obtaining a set of tags from a source of interest comprising the steps of:
   (a) providing a double-stranded cDNA, prepared from mRNA,
   (b) cleaving said double-stranded cDNA with a punctuating restriction endonuclease providing a cDNA fragment,
   (c) ligating to said cDNA fragment a 5' adapter comprising a recognition sequence for a type IIs restriction endonuclease which allows DNA cleavage at a site in the cDNA fragment distant from the recognition sequence for a type IIs restriction endonuclease providing a first cDNA construct, (d) cleaving said first cDNA construct with said type IIs restriction endonuclease providing a second cDNA construct, (e) ligating to said second cDNA construct a 3' adapter, thereby producing a recognition sequence for a punctuating endonuclease located 3' adjacent to said second cDNA construct, providing a third cDNA construct, (f) digesting said third cDNA construct with said punctuating restriction endonuclease providing a set of tags comprising cDNA sequences, and (g) determining the nucleotide sequences of said set of tags.

* * * * *

SEQUENCE LISTING

<160> NUMBER OF SEQ ID NOS: 8

<210> SEQ ID NO 1
<211> LENGTH: 66
<212> TYPE: DNA
<213> ORGANISM: Artificial Sequence
<220> FEATURE:
<223> OTHER INFORMATION: Synthetic

<400> SEQUENCE: 1
gccgaattcg aaacggccga tgtcttcagt cgacctgtat ggcccttagc attagggctg    60
tgcagc                                                                66

<210> SEQ ID NO 2
<211> LENGTH: 68
<212> TYPE: DNA
<213> ORGANISM: Artificial Sequence
<220> FEATURE:
<223> OTHER INFORMATION: Synthetic

<400> SEQUENCE: 2

```
cggctgcaca gccctaatgc taagggccat acaggtcgac tgaagacatc ggccgtttcg      60
aattcggc                                                               68
```

<210> SEQ ID NO 3
<211> LENGTH: 62
<212> TYPE: DNA
<213> ORGANISM: Artificial Sequence
<220> FEATURE:
<223> OTHER INFORMATION: Synthetic

<400> SEQUENCE: 3

```
ccggagatct gcggccgctc gactgcaaga cgacagtcta acgcaaagga aaggctaac      60 tg                                                                     62
```

<210> SEQ ID NO 4
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (63)..(64)
<223> OTHER INFORMATION: n = a, t, g, or c

<400> SEQUENCE: 4

```
cagttagcct tttcctttgc gttagactgt cgtcttgcag tcgagcggcc gcagatctcc      60 ggnn                                                                   64
```

<210> SEQ ID NO 5
<211> LENGTH: 39
<212> TYPE: DNA
<213> ORGANISM: Artificial Sequence
<220> FEATURE:
<223> OTHER INFORMATION: Synthetic

<400> SEQUENCE: 5

```
aattcagata aggcgcgccg atgtcttcat ttgtgcagc                             39
```

<210> SEQ ID NO 6
<211> LENGTH: 37
<212> TYPE: DNA
<213> ORGANISM: Artificial Sequence
<220> FEATURE:
<223> OTHER INFORMATION: Synthetic

<400> SEQUENCE: 6

```
cggctgcaca aatgaagaca tcggcgcgcc ttatctg                               37
```

<210> SEQ ID NO 7
<211> LENGTH: 16
<212> TYPE: DNA
<213> ORGANISM: Artificial Sequence
<220> FEATURE:
<223> OTHER INFORMATION: Synthetic

<400> SEQUENCE: 7

```
ccggagttta aacagc                                                      16
```

<210> SEQ ID NO 8
<211> LENGTH: 22
<212> TYPE: DNA
<213> ORGANISM: Artificial Sequence
<220> FEATURE:

```
-continued

<223> OTHER INFORMATION: Synthetic
<220> FEATURE:
<221> NAME/KEY: misc_feature
<222> LOCATION: (21)..(22)
<223> OTHER INFORMATION: n = a, t, g, or c

<400> SEQUENCE: 8
ggccgctgtt taaactccgg nn                                              22
```